United States Patent [19]

Rathemacher

[11] Patent Number: 4,614,076
[45] Date of Patent: Sep. 30, 1986

[54] FLEXIBLE PACKAGING APPARATUS AND METHOD

[75] Inventor: John W. Rathemacher, Laurence Harbor, N.J.

[73] Assignee: Becton, Dickinson and Company, Franklin Lakes, N.J.

[21] Appl. No.: 737,306

[22] Filed: May 23, 1985

[51] Int. Cl.⁴ .............................................. B65B 31/00
[52] U.S. Cl. ...................................... 53/433; 53/454; 53/511; 53/560
[58] Field of Search ................. 53/453, 433, 454, 511, 53/559, 560, 546

[56] References Cited

U.S. PATENT DOCUMENTS

| | | | |
|---|---|---|---|
| 3,397,508 | 8/1968 | Stroop | 53/559 |
| 3,418,140 | 12/1968 | Fisher | 53/559 X |
| 3,805,486 | 4/1974 | Mahaffy et al. | 53/559 |
| 4,034,536 | 7/1977 | Mahaffy et al. | 53/453 X |
| 4,265,070 | 5/1981 | Mainberger et al. | 53/559 X |

Primary Examiner—Horace M. Culver
Attorney, Agent, or Firm—Robert P. Grindle

[57] ABSTRACT

Methods and apparatus are provided for the continuous and rapid production of a plurality of flexible packages containing a non-solid substance such as an ointment, by continuously forming and vacuum sealing the packages from two webs of material in the nip of cooperating roller surfaces. The packages each contain a precise quantity of medication which may be, for example, the kind of medication which is self-administered by the user by transdermal application. The method and apparatus herein joins together two specially prepared webs of material continuously drawn from supply rolls while at the same time incorporating and vacuum sealing a desired quantity of the medication therebetween.

9 Claims, 7 Drawing Figures

FLEXIBLE PACKAGING APPARATUS AND METHOD

BACKGROUND AND STATEMENT OF THE INVENTION

This invention relates generally to methods and apparatus for producing flexible packaging. More particularly, this invention relates to methods and apparatus for the continuous production of flexible packaging wherein each individual package contains a vacuum sealed controlled quantity of a non-solid substance. Representative of such substances are ointments and salves, for example.

It is the nature of flexible packaging of the type contemplated herein that two webs are joined together and prior to the joining, a vacuum is applied so as to provide the desired sealed evacuated flexible package as the resulting or ultimate product. In providing such packaging in the past, it has been appropriate to join together the webs in a horizontal relationship along a production line and to continuously form across the breadth of the webs being joined together a plurality of packages simultaneously. In doing so, a manifold applies to the webs a vacuum immediately prior to the two webs being sealed and the individual packages cut from the joined webs. Such procedures provide a desirable package with an appropriate quantity of the material contained therein under the proper sealed evacuated conditions. However, such procedures are cumbersome and time consuming in this day of producing multiple quantities of flexible packaging for various applications.

It is important that a precise controlled quantity of material be contained in each individual package if, for example, the ointment or salve is a medication requiring a precise controlled quantity for later medical application to a patient. Such applications include, for example, transdermal medication in which a flexible package includes a special membrane with an adhesive surface which may be applied to the skin of a patient for a controlled administration of a medication over a period of time. Such flexible packages include a peel-off film over the adhesively surfaced membrane which the user peels off immediately prior to applying the package to his skin.

As will be appreicated, such packages must have a precise controlled quantity of an ointment containing the medication so as to provide the proper amount of medication over a period of time. Supplying and joining the webs appropriate for producing such packaging together in a horizontal flat orientation and going through this sequential application of vacuum, insertion of the material involved, and the sealing of the various packages together is a somewhat cumbersome process requiring a rather slow output or production of such flexible packages.

By contrast, with the invention herein, methods and apparatus are provided for the continuous and rapid production of a plurality of such flexible packages containing a non-solid material by joining the two webs together in the nip of sealing rolls. That is, a plurality of such packages are formed simultaneously across the width of the webs being joined together in the roller nip which cooperate to provide automatically and simultaneously the formation, evacuation and sealing of each individual flexible package in the webs. By utilizing a joining together in the nip of cooperating rolls, a much larger quantity of flexible packages may be produced on a continuous basis in a much more simplified manner. The invention contemplates the use of cooperating sealing rollers in which one roll includes pockets for forming the individual flexible packages cooperating with a second roll which provides a proper pressure at the nip of the rolls in order to form the individual packages across the width of the webs being joined.

It has been found that by the use of the specific kind of cooperating rollers, in accordance with this invention, that no special vacuum application need be made and that the flexible packages are formed automatically and continuously in the cooperating roller nip. In doing so, individual quantities of the medication, salve or ointment to be incorporated into the packages is applied to one web immediately prior to the cooperating roller nip. Thereafter, the individual quantities on the web pass into the roller nip and are incorporated into the individual packages. The individual quantities of medication move into the related pockets on the opposed roller at the cooperating nip so as to provide automatically between the webs being joined an individual evacuated pocket containing the ointment or material to be contained in the packages. As the individual pockets pass into the nip, the two webs are joined together and sealed automatically around the rim of the pockets, as will be discussed in more detail below.

It will be understood by practitioners-in-the-art, that the webs contain thermoplastic resin materials which may be joined and sealed under the application of heat and pressure. The crimp rolls which cooperate to provide the sealed packaging on a continuous basis are heated in order to provide the appropriate sealing of the two webs together during the simultaneous forming, evacuation and sealing of the flexible packages. Once the two webs are joined together, the webs are slit longitudinally into a plurality of strips each containing therealong in spaced fashion a plurality of formed and sealed flexible packages. Subsequent to the slitting of the individual elongated strips from the originally joined webs, the web strips pass through a knife station which cuts the individual packages from their elongated web strip for collection and inspection.

Before describing this invention in more detail, it may be well to note that the flexible packaging procedures involved herein apply to a variety of different materials which may be packaged, as long as they contain a liquid component. That is, ointments, salves and even oils may be contained within the flexible packaging herein, as long as the material involved will, when dropped on the web and prior to being sealed in the roller nips, hold a momentary self-contained body until such time as the material is properly joined in the evacuated flexible packaging formed by the methods and apparatus herein. It will be understood, furthermore, that a variety of different film materials comprised of thermoplastics may be utilized in the processing of the invention herein for forming the webs which are joined together to produce the flexible packaging. For example, polyvinyl chloride, polyvinylidene chloride, polyesters, polyethylene and polypropylene are all materials which may be utilized.

With the foregoing and additional objects in view, this invention will now be described in more detail, and other objects and advantages thereof will be apparent from the following description, the accompanying drawings, and the appended claims.

As purely illustrative of apparatus which may be used for carrying out the process of this invention, one may note the attached drawings in which a schematic illustration of apparatus for carrying out the invention is shown together with a representative example of one of the crimp rolls which cooperate to produce the flexible packaging of the invention. Also, a representative package which may be formed in accordance with this invention is shown and described.

DESCRIPTION OF THE DRAWINGS

FIG. 3 is a sectional view taken along lines 3—3 of FIG. 2;

FIG. 4 is a sectional view taken along lines 4—4 of FIG. 2;

DETAILED DESCRIPTION OF THE INVENTION

Figure 1:
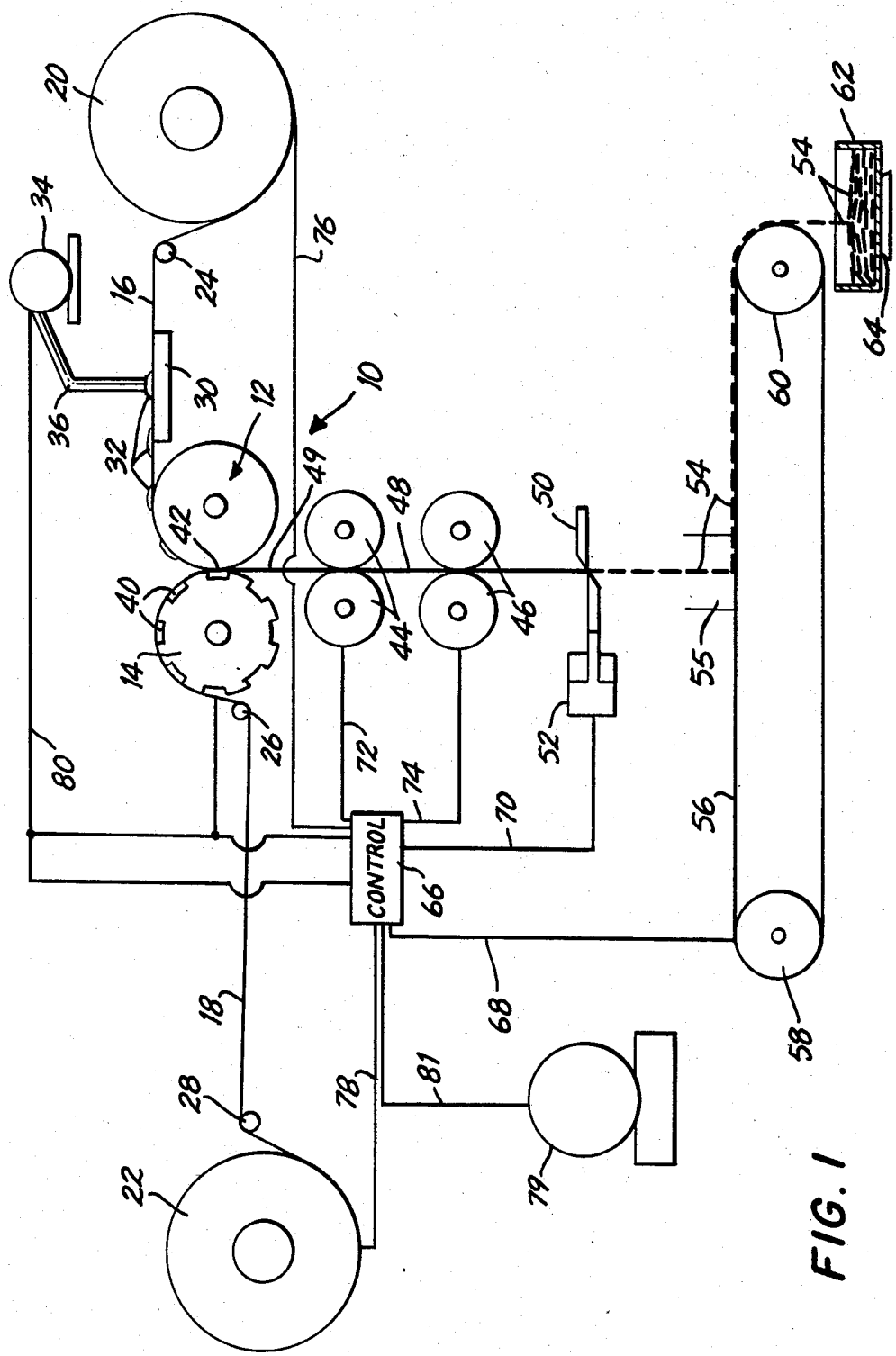
FIG. 1 is a schematic illustration of apparatus for carrying out this invention.

Referring to the drawings in which like reference characters refer to like parts throughout the several views thereof a roller type apparatus for producing on a continuous basis, evacuated flexible packaging containing materials with a liquid component therein is shown generally at 10. Thus, cooperating crimp rolls 12, 14 form from webs 16, 18, a joined web 49 at cooperating nip 42. The web 16 is taken from a supply roll 20 with web 16 passing over a guide roll 24 prior to passing through station 30 where quantities 32 of an ointment, for example, to be incorporated into the plurality of packages is deposited on web 16 from an ointment supply 34 which passes through tubes 36 for the deposit of the material 32 on web 16. Although not shown, it will be understood that a plurality of material deposits 32 are deposited simultaneously across the width of web 16. Thereafter, the deposited materials 32 pass to the cooperating nip 42 between rolls 12, 14 wherein the material passes into cooperating spaces 40 on roll 14. The periphery of the pockets or spaces 40 on roll 14 serves as the border for the sealing of the material 32 between the webs 16, 18, as will be discussed in more detail below.

Web 18 is drawn from a supply roll 22 and passes over guide rolls 28, 26 prior to passing around the cooperating crimp roll 14. After passing through nip 42, the joined together web 49 containing a plurality of incorporated flexible evacuated sealed packages in accordance with this invention, passes to a pair of cooperating slitter rolls 44. The slitter rolls slit the web 49 into a plurality of longitudinal strips containing on a continuous spaced basis a plurality of the flexible packages produced in accordance with this invention.

Once the web passes through slitter rolls 44 for slitting the web across the transverse extent thereof, the web becomes a plurality of slit longitudinal webs 48 which pass through friction rolls 46 which serve to hold the slit webs 48 in proper alignment for feeding the webs to the knife station 50 wherein the individual longitudinal slits of the web are cut into individual packages 54 which drop into a guide station 55 on the top of conveyor 56. The belt of conveyor 56 passes over spaced apart rolls 58, 60 in a conventional manner. The conveyor 56 conveys the individual packages 54 to a receiving container 62 at station 64 wherein filled containers 62 are removed so that the individual packages may be inspected.

The knife station 50 operates under the action of a reversible cylinder 52 under control 66 through line 70. As will be appreciated by practitioners-in-the-art, all of the rolls in the apparatus described are driven by motor 79 through conventional belts and reduction gearing in order to provide the proper sequential operation and rotational speeds of the various rolls for controlling the web passing through the apparatus. Moreover, control 66 controls through line 80 the dispensing container 34 and the quantity of materials passing through the lines 36 to make the appropriate quantities and timing of the materials 32 on the top of web 16.

Figure 2:
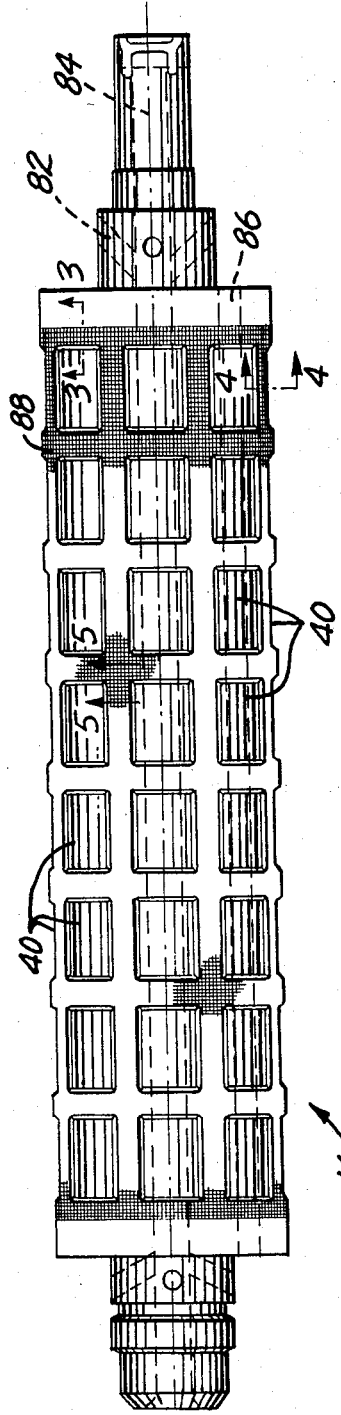
FIG. 2 is a longitudinal elevational view of one crimp roll for forming the flexible packages of the invention, and illustrating the plurality of pockets in the surface thereof for forming the individual packages.

As will be understood by practitioners-in-the-art, control 66 also controls through lines 76, 78, the required braking necessary for supply rolls 20, 22 respectively so that the webs 16, 18 are held in proper alignment for feeding to the cooperating crimp rolls 12, 14. Control 66, in turn, through lines 72, 74 controls the proper rotational speeds of the slitter rolls 44 and the cooperating friction rolls 46. Control 66 through line 68 controls the speed of conveyor 56 for the proper takeoff of the final products 54 from station 55 to the waiting containers 62. If required, roll 26 may be in the form of a preheat roller in order to raise the temperature of web 18 prior to the entry of web 18 onto heated crimp roll 14 so that the thermoplastic material is in the proper form for properly joining and sealing to web 16 at nip 42. As shown in FIG. 2, a representative crimp roll 14 may have a plurality of pockets 40 along the longitudinal extent thereof with eight such pockets formed around the circumference thereof. Thus, eight packages may be formed in the cooperating nip 42 between crimp rolls 12, 14 at any one moment during the rotation of a roll 14. Under these circumstances, as will be appreciated by practitioners-in-the-art, a large quantity of flexible packages properly evacuated and sealed may be produced simultaneously and continuously with the operation of the apparatus of the invention. As can be seen in FIG. 2, on the outer surface of roll 14 there may be a knurled surface 88. This knurled surface is only shown partially, for clarity, on roll 14 in FIG. 2. The knurled surface may cooperate with a knurled surface on roll 12 in order to provide a positive drive at all times between the two cooperating rolls. In this manner, the deposited materials 32 will always be in proper alignment with the pockets 40 so as to provide the proper sealed and evacuated flexible packages on a continuous basis at the cooperating roller nip 42.

Roll 14 may have a plurality of longitudinal passages 84, 86 in order to introduce heat into the cooperating rolls. That is, roll 14 may have passing therethrough heated water in one form of arrangement. However, it may be appropriate to use electrodes inserted in the longitudinal passages 84, 86 of the roll with the electrodes making a contact through a wiper arrangement as the roll 14 rotates, all well known in the art.

FIGS. 3 and 4 show sectional views of portions of the knurled surface of roll 14. Thus, dimension 94 may be, as representative of specific dimensions on the knurled surface, 0.0318 inches. The sharp points 90 may be polished to a radius of 0.002-0.005 inches. The angle 92 may be 120°+ one degree. The dimension 96 in FIG. 4 may be, for example, 0.0316 inches. The cooperating knurled surfaces 88 on rolls 12 and 14 may be arranged so that one roll will have the center line of the tooth on the center line of the pocket on the surface of the roll and the other roll with the bottom of the tooth on the center line of the pocket. For this reason, there is always a cooperating positive drive between the rolls. Thus, there is no mis-alignment between the quantities 32 of material on web 16 with the pockets 40 on roll 14.

Figure 5:
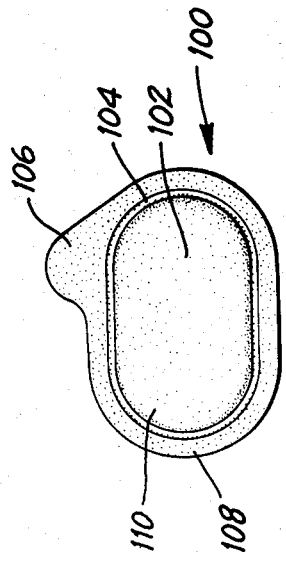
FIG. 5 is a sectional view taken along lines 5—5 of FIG. 2.

As can be seen in FIG. 2, roll 40 is a solid roll formed with its own drive shaft in one solid piece. This in turn helps to eliminate any problems involved with misalignment between the crimp rolls at the cooperating roller nip. There may be, for example, 460 teeth around the circumference of roll 14. The groove is cut as a helix on the right-hand on one roll and on the left hand on the other roll. FIG. 5 shows the configuration of the pocket 40 on the roll surface. The upper edge 98 of pocket 40 is beveled so as to provide a proper cooperation between the web 18 passing around the surface of roll 14 and the individual pockets 40. The bevel may be, for example, 1/32 of an inch in width with an angle from the top surface of the roll being about, for example, 20°. The depth of the pockets 40 may be, for example, between 3/16 to 5/16 inches.

Figure 6:
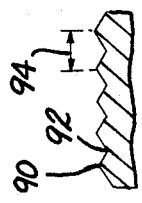
FIG. 6 is a plan view of one form of flexible package produced in accordance with the methods and apparatus of the invention.

While the pockets shown on the roll 14 in FIG. 2 are rectangular in shape, it will be understood that the pockets 40 may be of a variety of different configurations in order to provide appropriately dimensioned and shaped packages, as required. FIG. 6 is representative of a flexible package produced in accordance with the methods and apparatus of the invention. As can be seen, the package 100 is configured in a generally oval shape with a tab 106 which is used as a guide tab for helping the user of a package 100 to grasp the peelable surface from the package in order to peel off and expose the membrane so that the medication may be exposed and applied to the skin of a patient for the slow dispensing of a medication from the package 100. The tab 106 is clearly shown outside the seal 104 formed around the center portion 102 containing the medication or other material contained in package 100. Outside the seal 104 is a border 108.

Figure 7:
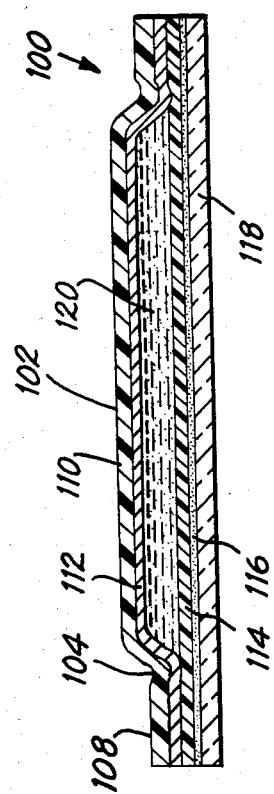
FIG. 7 is an enlarged sectional view of the package illustrated in FIG. 6 and showing the individual layers of material utilized to form the package.

Referring to FIG. 7, an enlarged longitudinal sectional view of a representative package produced in accordance with the methods and apparatus of the invention is shown. This package is the kind of package which may be utilized by the user to provide a uniform dispensing and dosing of a medication contained in the central portion 120 of the package through the skin of the user. Thus, as shown in FIG. 7, the package has a border 108 outside the sealed area 104 with a central container portion 120 of the package. The package includes a film backing 110 which provides appropriate "body" for the package. Adhered to film backing 110 is a foil 112 which serves as an occlusive material for the combined laminate 110, 112. That is, foil 112 serves as a barrier to prevent the passage of a material contained in the central portion 120 out through the film backing 110.

The film backing may be, for example, polyethylene film. The films 110, 112 may be, for example, the web 16 as shown in FIG. 1. Forming web 18, for example, is a membrane film 114 which may be a transdermal material for allowing the passage of a medication contained in space 120 therethrough. Formed on the top surface of membrane 114 is an adhesive 116 to be described in more detail below. Finally, on top of adhesive 116 is a peelable layer 118 which is removed for use of the package if it is to be used as a transdermal dispensing package as described previously here. The clear peelable material may be, for example, a polyester. The adhesive layer may be, for example, a silicon based adhesive which would be appropriate for allowing the medication in container 120 to pass through membrane 114 to the skin once the adhesive layer 116 is exposed and the package adhered to the skin of the user.

As will be understood by practitioners-in-the-art, the various films will be selected depending upon the ultimate use of the flexible packages, in accordance herewith. It would be understood that the peelable film 118 may serve to open the package if the contents in container 120 were to be dispensed all at once by the user, depending upon what the contents are. For example, the flexible package may simply be a container for an ointment to be dispensed in individual portions to the user who merely opens the package by peeling off the peelable film 118 to expose an opening, for example, in the film 114. Under these circumstances, the film 114 would not be in the form of a membrane.

Accordingly, there is provided, as will be apparent from the foregoing, methods and apparatus for producing a plurality of flexible packages on a continuous rapid basis. Moreover, the flexible packages are individually formed with a controlled quantity of material, sealed, and evacuated simultaneously to provide the individual self-contained packages. The apparatus and methods herein are particularly appropriate for producing automatically transdermal medication packages so that a user may peel a film from the individual packages and adhere the packages to the skin for providing a regulated quantity of a medication through the skin to treat an individual. The arrangement herein provides for evacuation of a plurality of individual packages simultaneously without the separate application of a vacuum. The cooperating controlled operation of the crimp rolls, in accordance herewith, allows for a plurality of such packages to be produced simultaneously in evacuated form with precise coordinated sealing of each individual package. Thus, large quantities of such packages may be produced much more rapidly than was the case previously in the same amount of time.

While the methods and apparatus herein disclosed form preferred embodiments of the invention, this invention is not limited to those specific methods and apparatus, and changes can be made therein without departing from the scope of the invention which is defined in the appended claims.

What is claimed is:

1. Apparatus for the controlled simultaneous forming, filling, evacuating and sealing of a plurality of flexible packages containing a material with a liquid component continuously in a roller nip; characterized by
   (a) a first supply roll for continuously supplying a first web for forming a first side of the flexible packages to be formed;
   (b) a second supply roll for continuously supplying a second web for forming a second side of the flexible packages to be formed;
   (c) a pair of heated crimp rolls positioned in cooperating engagement to continuously receive and join said first and second webs in a flexible package forming nip while simultaneously evacuating air from packages so formed in said nip;

(d) a filling material station positioned between said first supply roll and said nip for depositing a plurality of spaced apart quantities of filling material for said packages on said first web;

(e) rotary cutting means positioned after said package forming nip for continuously receiving said joined web and continuously severing said joined web into a plurality of flexible packages;

(f) first power means connected to said first and second supply rolls and said crimp rolls for the driving thereof;

(g) second power means connected to said cutting means for the driving thereof; and (h) control means connected to said first and second power means for the controlled operation thereof.

2. The apparatus of claim 1, further characterized by (a) one of said crimp rolls includes a plurality of pockets spaced apart circumferentially and longitudinally over the surface thereof; and (b) said filling station is controlled by said control means to deposit quantities of said material on said continuously moving first web simultaneously in spaced apart fashion across the width of said first web and intermittently along the longitudinal extent of said continuously moving first web;

(c) whereby said deposited quantities of said material on said first web mate with said pockets on said one crimp roll in said flexible package forming nip.

3. The apparatus of claim 1, further characterized by (a) a pair of cooperating friction rolls positioned between said flexible package forming nip and said cutting means for continuously receiving said joined first and second webs; and (b) a pair of cooperating rotary slitting rolls positioned in the joined web path between said nip and said friction rolls;

(c) whereby said slitting rolls continuously slit said joined web into a plurality of continuously moving longitudinal strips of formed spaced apart flexible packages;

(d) said cutting means cutting said longitudinal strips into a plurality of flexible packages.

4. A flexible package formed by the process of claim 1, characterized by (a) said first web for said first supply roll is a laminate comprised of thermoplastic film for the backing layer for said flexible packages, and an inner layer of foil; and (b) said second web for said second supply roll is a laminate comprised of an outer layer of a peelable thermoplastic film for opening said flexible packages, and adhesive inner layer for adhering said peelable outer layer.

5. The package of claim 4, further characterized by (a) said second web includes an inner membrane film layer on the side of said adhesive inner layer opposite said peelable film layer allowing controlled passage of the contents of said package therethrough.

6. The package of claim 5, further characterized by (a) the contents of said package is a cream containing medication for continuous dispensing through said membrane and adhesive layers to the user's skin.

7. A continuous process for the controlled simultaneous forming, filling, evacuating and sealing a plurality of flexible packages containing a material with a liquid component in a roller nip; characterized by (a) continuously supplying in a first supplying step a first web of material for forming a first side of the flexible packages to be formed;

(b) continuously supplying in a second supplying step a second web of material for forming a second side of the flexible package to be formed;

(c) utilizing a pair of heated crimp rolls positioned in cooperating engagement for receiving and joining said first and second webs from said first and second supplying steps in a flexible package forming nip;

(d) said receiving and joining step simultaneously causing evacuation of ambient air from packages formed thereby;

(e) prior to said utilizing step, depositing, a plurality of spaced apart quantities of filling material for said packages on said first web from said first supplying step;

(f) passing said web from utilizing step to a cutting means;

(g) cutting said web from said passing step into a plurality of filled flexible packages.

8. The process of claim 7, further characterized by (a) said utilizing step being carried out with one of said crimp rolls having a plurality of pockets spaced apart circumferentially and longitudinally over the surface thereof; and (b) said depositing step being carried out so that quantities of said material are deposited on said first web simultaneously in spaced apart fashion across the width of said first web and intermittently along the longitudinal extent of said continuously moving first web;

(c) whereby said deposited quantities of said material on said first web mate with said pockets on said one crimp roll in said flexible package forming nip.

9. The process of claim 7, further characterized by (a) prior to said cutting step, continuously slitting said web from said utilizing step into a plurality of continuously moving longitudinal strips of joined together flexible packages.

* * * * *